US012808822B2

(12) United States Patent
Quadling et al.

(10) Patent No.: US 12,808,822 B2
(45) Date of Patent: Nov. 24, 2026

(54) X-RAY COMPUTED TOMOGRAPHY (CT) SCANNING USING A LINE ARRAY DETECTOR

(71) Applicants: Mark S. Quadling, Plano, TX (US); Henley S. Quadling, Dallas, TX (US)

(72) Inventors: Mark S. Quadling, Plano, TX (US); Henley S. Quadling, Dallas, TX (US)

(73) Assignee: Sentient Reality Dental, LLC, Dallas, TX (US)

( * ) Notice: Subject to any disclaimer, the term of this patent is extended or adjusted under 35 U.S.C. 154(b) by 0 days.

(21) Appl. No.: 18/597,398

(22) Filed: Mar. 6, 2024

(65) Prior Publication Data

US 2024/0298988 A1 Sep. 12, 2024

Related U.S. Application Data

(60) Provisional application No. 63/450,536, filed on Mar. 7, 2023.

(51) Int. Cl.

| | |
|---|---|
| ***G01N 23/046*** | (2018.01) |
| ***A61B 6/00*** | (2006.01) |
| ***A61B 6/03*** | (2006.01) |
| ***A61B 6/04*** | (2006.01) |
| ***A61B 6/06*** | (2006.01) |

(Continued)

(52) U.S. Cl.

CPC ........... *G01N 23/046* (2013.01); *A61B 6/032* (2013.01); *A61B 6/035* (2013.01); *A61B 6/0407* (2013.01); *A61B 6/06* (2013.01); *A61B 6/4078* (2013.01); *A61B 6/4085* (2013.01); *A61B 6/4233* (2013.01); *A61B 6/4435* (2013.01); *A61B 6/4452* (2013.01); *A61B 6/4476* (2013.01);

(Continued)

(58) Field of Classification Search

CPC ....... A61B 6/032; A61B 6/035; A61B 6/4078; A61B 6/42; A61B 6/4208; A61B 6/4233; A61B 6/44; A61B 6/4429; A61B 6/4435; A61B 6/4452; A61B 6/4476; A61B 6/51; G01N 23/046; G01N 23/10; G01N 23/18

USPC ... 378/10, 15, 19, 20, 38–40, 53–55, 57, 58, 378/62, 146, 189

See application file for complete search history.

(56) References Cited

U.S. PATENT DOCUMENTS 4,989,225 A * 1/1991 Gupta .................. G01N 23/046 378/10

5,023,895 A * 6/1991 McCroskey ......... G01N 23/046 378/177

(Continued)

*Primary Examiner* — Allen C. Ho

(74) *Attorney, Agent, or Firm* — David H. Judson

(57) ABSTRACT

An apparatus and method for X-Ray CT scanning of an object, such as a dental item. The apparatus includes a line array detector, such as a time-delay integration (TDI) camera. The sample to be imaged is positioned between the x-ray source and the detector. In operation, X-rays from the x-ray source are collimated into a wedge-shaped beam, which is then passed through the sample as the detector reciprocates along an arc to generate a plurality of line images. A first subset of the plurality of line images are assembled into a first 2D image, after which an $n^{th}$ subset of the plurality of line images are assembled into an $n^{th}$ 2D image, wherein a total number of subsets and corresponding 2D images is more than 2. The corresponding 2D images are processed into a 3D volumetric representation of the sample.

19 Claims, 16 Drawing Sheets

(51) Int. Cl.

| | |
|---|---|
| ***A61B 6/40*** | (2024.01) |
| ***A61B 6/42*** | (2024.01) |
| ***A61B 6/51*** | (2024.01) |
| ***G01N 23/10*** | (2018.01) |
| ***G01N 23/18*** | (2018.01) |

(52) U.S. Cl.

CPC .................. *A61B 6/51* (2024.01); *A61B 6/54* (2013.01); *G01N 23/10* (2013.01); *G01N 23/18* (2013.01)

(56) References Cited

U.S. PATENT DOCUMENTS

| | | | | |
|---|---|---|---|---|
| 5,119,408 | A * | 6/1992 | Little | G01N 23/046 378/10 |
| 5,228,071 | A * | 7/1993 | Kamata | G01N 23/046 378/62 |
| 6,104,776 | A * | 8/2000 | Oikawa | G01N 23/20025 378/57 |
| 6,148,058 | A * | 11/2000 | Dobbs | A61B 6/587 378/10 |
| 6,459,760 | B1 * | 10/2002 | D'Ambrosio | G01N 23/04 378/207 |
| 6,470,068 | B2 * | 10/2002 | Cheng | A61B 6/0478 378/10 |
| 6,504,898 | B1 * | 1/2003 | Kotler | G21K 5/10 378/68 |
| 6,553,094 | B1 * | 4/2003 | Bernardi | G01N 23/046 378/57 |
| 6,618,465 | B2 * | 9/2003 | Mohr | G01N 23/04 378/146 |
| 6,624,425 | B2 * | 9/2003 | Nisius | G01N 23/046 250/363.01 |
| 6,909,768 | B2 * | 6/2005 | Takagi | G01N 23/046 378/62 |
| 6,940,948 | B1 * | 9/2005 | Tretiakov | A61B 6/00 378/146 |
| 7,016,465 | B2 * | 3/2006 | Kamegawa | G01N 23/046 378/19 |
| 7,082,182 | B2 * | 7/2006 | Zhou | G01N 23/046 378/10 |
| 7,187,752 | B2 * | 3/2007 | Kotler | G21K 5/04 378/68 |
| 7,356,115 | B2 * | 4/2008 | Ford | G01N 23/046 378/57 |
| 7,492,862 | B2 * | 2/2009 | Bendahan | G01V 5/281 378/57 |
| 7,508,908 | B2 * | 3/2009 | Hu | G01N 9/24 378/57 |
| 7,551,714 | B2 * | 6/2009 | Rothschild | G01N 23/046 378/45 |
| 7,639,777 | B2 * | 12/2009 | Warner | G21K 1/025 378/19 |
| 7,672,426 | B2 * | 3/2010 | Seppi | G01N 23/046 378/57 |
| 7,729,469 | B2 * | 6/2010 | Kobayashi | A61B 6/4482 378/69 |
| 7,792,242 | B2 * | 9/2010 | Kamegawa | G01N 23/046 378/207 |
| 8,068,579 | B1 * | 11/2011 | Yun | G01N 23/046 378/4 |
| 9,110,004 | B2 * | 8/2015 | Feser | G01N 23/046 |
| 9,121,809 | B2 * | 9/2015 | Cox | G01N 23/04 |
| 11,071,506 | B1 * | 7/2021 | Szczykutowicz | A61B 6/032 |
| 11,262,318 | B2 * | 3/2022 | Salamon | G01N 23/046 |
| 11,474,052 | B2 * | 10/2022 | Safai | G01N 23/18 |
| 11,504,077 | B2 * | 11/2022 | Bambot | A61B 6/032 |
| 11,633,145 | B2 * | 4/2023 | Pogue | G01N 23/046 378/4 |
| 11,639,904 | B2 * | 5/2023 | Ohbayashi | G01N 23/046 378/19 |
| 11,656,189 | B2 * | 5/2023 | Ueki | G01N 23/046 378/10 |
| 11,808,718 | B2 * | 11/2023 | Harada | G01N 23/046 |
| 11,821,851 | B2 * | 11/2023 | Niizaka | G01N 23/046 |
| 11,821,860 | B2 * | 11/2023 | Omlor | G01N 23/046 |
| 12,007,340 | B2 * | 6/2024 | Nakayama | G01N 23/046 |
| 12,085,540 | B1 * | 9/2024 | Zhang | G01N 23/046 |
| 12,123,852 | B1 * | 10/2024 | Hu | G01N 33/24 |
| 12,392,737 | B2 * | 8/2025 | Caliskan | G01N 23/20025 |
| 12,517,068 | B2 * | 1/2026 | Bendahan | G01N 23/046 |
| 12,618,998 | B2 * | 5/2026 | Procter | G01N 23/046 |

* cited by examiner

X-RAY COMPUTED TOMOGRAPHY (CT) SCANNING USING A LINE ARRAY DETECTOR

BACKGROUND OF THE INVENTION

Computed Tomography (CT) scanning is a well-established technique for the tomographic reconstruction of volumes using X-Ray projection images. The first commercially available unit was created in 1972 by Godfrey Hounsfield.

The current system in use in dentistry today is the variant of CT scanning known as Cone Beam CT scanning (CBCT). It has the advantage over conventional ray beam (slice or helical path) CT scanning by offering faster acquisition times as well as lower radiation doses to the patient. However, it also suffers from the inherent reduced quality of CBCT versus slice based CT scanning for a number of reasons. Firstly, in terms of the theory, it can be shown that CBCT can only be solved approximately, so in general the reconstructed models are not as detailed as typically achieved with fan beam CT. There are a number of iterative algebraic methods which do produce better results compared to, for example, the approximate FDK method, but they are computationally complex and take a significant amount of time to generate. Secondly, because of the broad cone of radiation, there is increased scatter which translates to more noise in the reconstructed volumes. There is also less contrast, and CBCT is more susceptible to motion artifacts as well compared to fan beam CT scanning. An additional issue with current dental CBCT scanners is the use of X-Ray sources with a large spot size of 0.2-0.5 mm or even larger in some cases. A larger spot size results in a penumbra or "softening" of edges on the order of the spot size.

Taking all the issues noted above, dental CBCT is currently unable to produce models accurate enough to be used, for example, for restorative dental purposes. For a restorative type application, a prepared tooth would need to be imaged and the surface extracted from the volume data. The poor resolution of a dental CBCT derived surface, compared to an intra-oral 3D scan for example, precludes the use of that surface to be used for the purpose of making a dental restoration.

Besides having all the current functionality of today's dental CBCT systems, an ideal dental CT system should be capable of performing the scanning required for dental CAD/CAM applications (such as crowns, veneers, implants, orthodontic appliances, etc.). Today, those functions have to be provided by a separate device (a 3D intra-oral camera) or through the taking of analog impressions. Such a process would be more accurate than the current analog and digital methods, because those methods are subject to user technique and other issues, such as incorrect tissue management or material issues in the case of the analog impression. Further, the improved performance of such a dental CT system should not be at the expense of greatly increased X-Ray dosage to the patient, and it should provide an easy experience for both user and dentist.

SUMMARY OF THE INVENTION

An apparatus and method for X-Ray CT scanning of an object, such as a dental item. The apparatus includes a line array detector, such as a time-delay integration (TDI) camera. The sample to be imaged is positioned between the x-ray source and the detector. The line array detector is associated with a first rotation stage, and wherein the sample is associated with a second rotation stage. In operation, X-rays from the x-ray source are collimated into a wedge-shaped beam, which is then passed through the sample as the detector reciprocates along an arc to generate a plurality of line images. A first subset of the plurality of line images are assembled into a first 2D image, after which an $n^{th}$ subset of the plurality of line images are assembled into an $n^{th}$ 2D image, wherein a total number of subsets and corresponding 2D images is more than 2. The corresponding 2D images are processed into a 3D volumetric representation of the sample. In a first embodiment, the $n^{th}$ subset of the plurality of line images is obtained by keeping the second rotation stage at a constant rotation angle while a rotation angle of the first rotation stage is varied for each line image; in a second embodiment, the $n^{th}$ subset is obtained by keeping the first rotation stage at a constant rotation angle while the rotation angle of the second rotation stage is varied for each line image.

The foregoing has outlined some of the more pertinent features of the subject matter. These features should be construed to be merely illustrative. Many other beneficial results can be attained by applying the disclosed subject matter in a different manner or by modifying the subject matter as will be described

BRIEF DESCRIPTION OF DRAWINGS

For a more complete understanding of the subject matter and the advantages thereof, reference is now made to the following descriptions taken in conjunction with the accompanying drawings, in which.

DETAILED DESCRIPTION OF THE INVENTION

Figure 1:
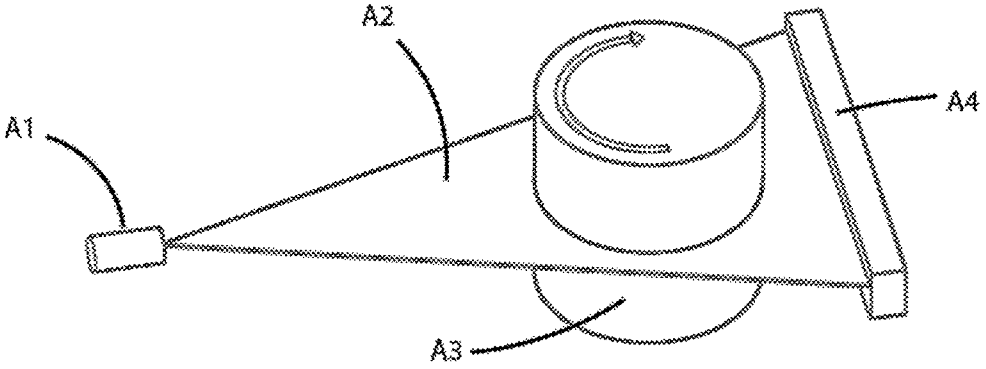
FIG. 1 depicts a conventional CT slice with ray beam.

By way of background, FIG. 1 depicts a simplified depiction of a CT slice technique. The large cylinder A3 represents the scan volume. The object to be scanned is contained entirely within this cylinder. The small cylinder A1 is an X-Ray source with a slit collimator so that only a thin beam is emitted from the source. The X-Ray beam A2 is emitted from the X-Ray source A1 as a diverging beam. Reference A4 is an imaging device that contains a number of detectors able to sample or image the X-Ray beam along the ray beam. A4 may be a line array camera for example, or may also be a two dimensional imaging device, such as a CCD or CMOS with a scintillator. The arrow shown on the scanning volume A3 represents how the scan volume rotates while being scanned. Alternatively and equivalently, the scan volume can remain stationary while the X-Ray source and line detector rotates around the sample. This is the normal way that CT scanning is performed in a medical setting. For ease of description the following assumes the equivalent case where the sample is rotating while the X-Ray source and line camera remain stationary. The conventional CT slice technique takes a series of images as the sample is rotated, then the volume within that slice can be reconstructed, for example, using a Filtered Back Projection technique. There may be as many as several hundred views taken in this way with a small angle rotation between each view.

Transverse Beam Scanning with a TDI Line Array Camera

In a first embodiment, which is now described, a system for performing CT scans uses a Time-Delayed Integration (TDI) X-Ray Line Camera. A representative device of this type is a Model C12300-461B manufactured by Hamamatsu Photonics, K.K., although the use of this particular device is not intended as a limitation. This particular device has a pixel count of 6144 (H) by 150 (V), pixel size of 48 microns by 48 microns, a scanning area of 293 mm wide by 7.2 mm, and read-out rate of no greater than 30 KHz.

A TDI camera is designed for high speed imaging of samples with a high sensitivity. Time Delay Integration is a scanning technology in which a frame transfer device produces a continuous video image of a moving object by means of a stack of linear arrays aligned with and synchronized to the motion of the object to be imaged in such a way that, as the image moves from one line to the next, the integrated charge moves along with it, providing higher resolution at lower light levels than is possible with a line-scan camera. In the case of X-Ray, the TDI enables high dynamic range in the image at lower X-Ray doses, and consequently is advantageous for in-vivo scanning.

Figure 2:
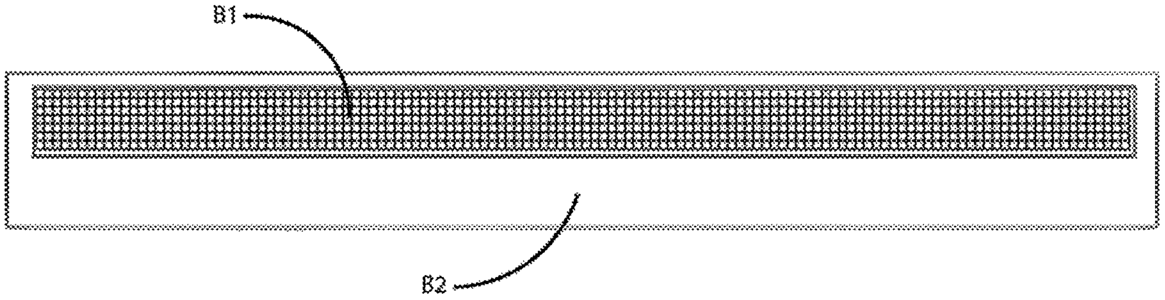
FIG. 2 depicts a Time-Delayed Integration (TDI) X-Ray line camera sensor.

FIG. 2 shows a simplified depiction of the TDI X-Ray Line scanner. The scanner comprises a body B2, and an imaging area B1. The imaging area may consist of a scintillator on top of an array of pixels on a CMOS or CCD device. During operation, an X-Ray image is projected onto the imaging area B1. In FIG. 2, the imaging area is shown as an array of 128 horizontal pixels by 7 vertical pixels. In practice, the actual resolution is much larger than this, but it has a similar aspect ratio with a much higher horizontal resolution (number of pixels in the horizontal direction) compared to the vertical resolution. More specifically, preferably the detector comprises a large number of pixels $n_x$ in a first direction, and a smaller number of pixels $n_y$ in a second direction orthogonal to the first direction, wherein $n_y$ is greater to or equal to 1, and $n_x$ is at least one order of magnitude larger than n.

Figure 3:
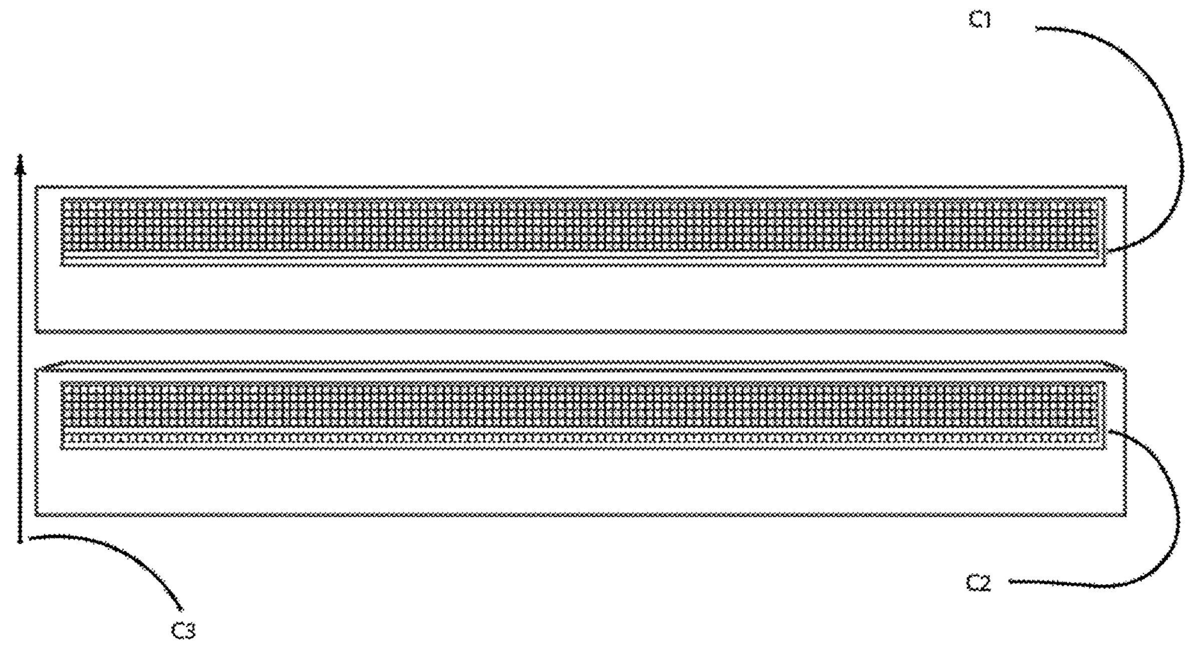
FIG. 3 depicts a TDI X-Ray scan.

Referring to FIG. 3, the TDI scan proceeds by moving the TDI scanner relative to the X-Ray beam that is incident on the imaging area. With reference to the drawing, consider the scanning motion from a point in time t1 to a later point in time t2. At time t1, a reference line in the X-Ray beam illuminates the row of pixels C1. At time t2, the X-Ray beam has moved upwards in the direction shown by the arrow C3, and that same reference line illuminates the row of pixels C2. Simultaneously, the TDI scanner moves the image that was accumulated in C1 to the row C2, so that now at time t2, the row of pixels C2 is illuminated by the same reference line in the X-Ray beam. This continues in this example for each of the 7 rows of the imaging pixels. The output at each point in time is the value of the pixels at row 7. By following this process, a relatively low intensity image can be reinforced, in this example, by imaging the same reference line 7 times, thus greatly improving the signal to noise ratio of the imaging reference line. It should be noted that even though the device has an area array of pixels, the final output at each point of time is only a single row of pixels. In this example, at each point in time a single row of 128 pixels is provided.

Given the manner in which TDI line scan operation is carried out, it can be seen that the motion required in FIG. 1 for conventional CT scanning is not possible because there the required motion is perpendicular to the motion needed for the correct operation of a TDI line scanner. Instead, and according to this disclosure, an alternative approach is provided so that the line camera can be used as required for the TDI operation by scanning transversally. This approach is now described.

Figure 4:
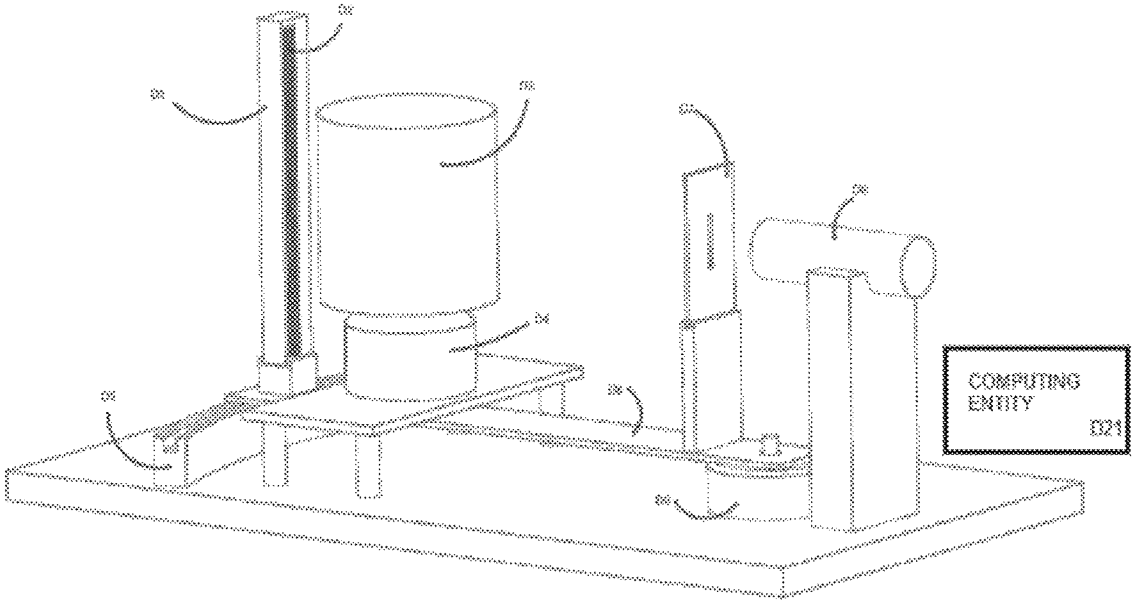
FIG. 4 depicts a system for transverse beam scanning with TDI line array camera according to a first embodiment of this disclosure.

In particular, FIG. 4 shows a system layout for a transverse beam scanner with a TDI line camera array according to a first embodiment of this disclosure. Here, D1 is a TDI Line Camera Array with D2 being the active imaging area. D3 is the scanning volume containing the sample. Because the scanning volume contains the sample, it is sometimes referred to herein as a sample holder. The scanning volume D3 and sample are rotated when necessary by a rotary stage D4, which in this example is capable of a full 360 degree rotation. D8 is an X-Ray source that generates a cone beam array of X-Ray radiation. D7 is a slit collimator, preferably manufactured from a dense material such as lead. D6 is a rigid arm to which is connected the slit collimator D7, as well as the TDI line array camera D1. The rigid arm D6 is connected to a rotary stage D9 that causes the rigid arm D6 (and attached slit collimator D7 and TDI line camera array D1) to rotate about the central axis of the rotary stage D9. D5 is a supporting rail for the rigid arm D6 to be supported as it rotates. A computer and hardware are used to control the two rotary stages, to control operation and intensity of the X-ray source D8, and to retrieve the line images from the TDI line camera array D1. The computer also contains software and a storage device used to perform the final volume reconstruction. The computer, typically comprising software executing in one or more hardware processors, is depicted as computing entity D21.

Figure 5:
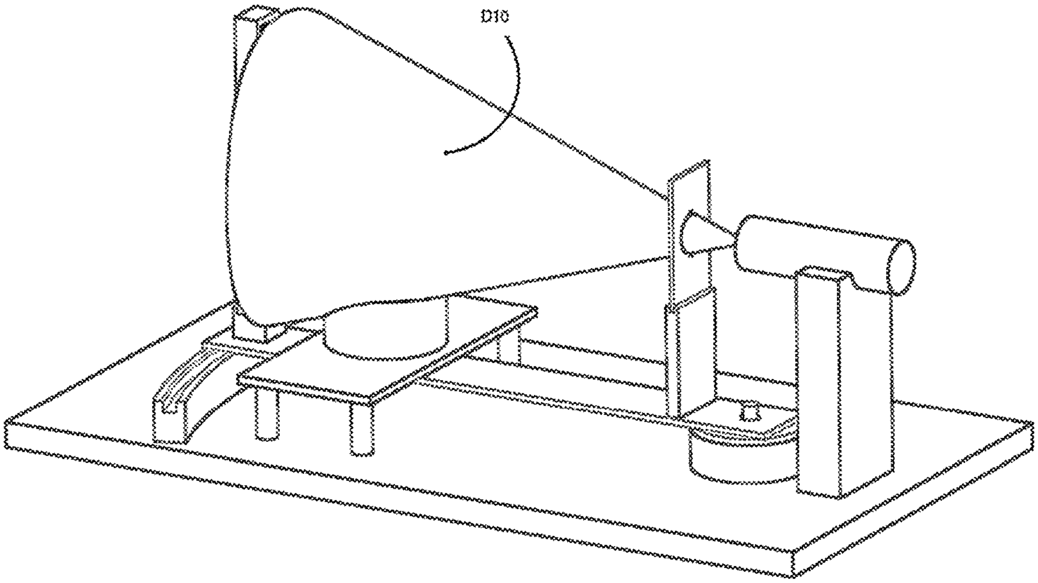
FIG. 5 depicts a full X-Ray cone beam pattern.

FIG. 5 shows the generated cone beam X-Ray radiation pattern when the X-Ray source D8 is energized. This would be the shape of the generated X-Ray beam if there were no collimator D7. FIG. 5 shows the collimator in place, however, in this particular case it is not functioning. It is valid to perform the scanning without a collimator, but there are two reasons why this is not advised. First, only a small section of the cone beam is imaged by the active scanning area D2, so the rest of the X-Ray does not contribute to the imaging of the sample but instead increases noise and error because those X-Rays may be diffracted internally by the sample and become incident on the imaging area as extra unwanted noise. Second, in the case where the sample is a live patient, the extra X-Ray radiation contained in the cone not incident on the imaging area is unnecessary and possibly damaging radiation to the patient.

Figure 6:
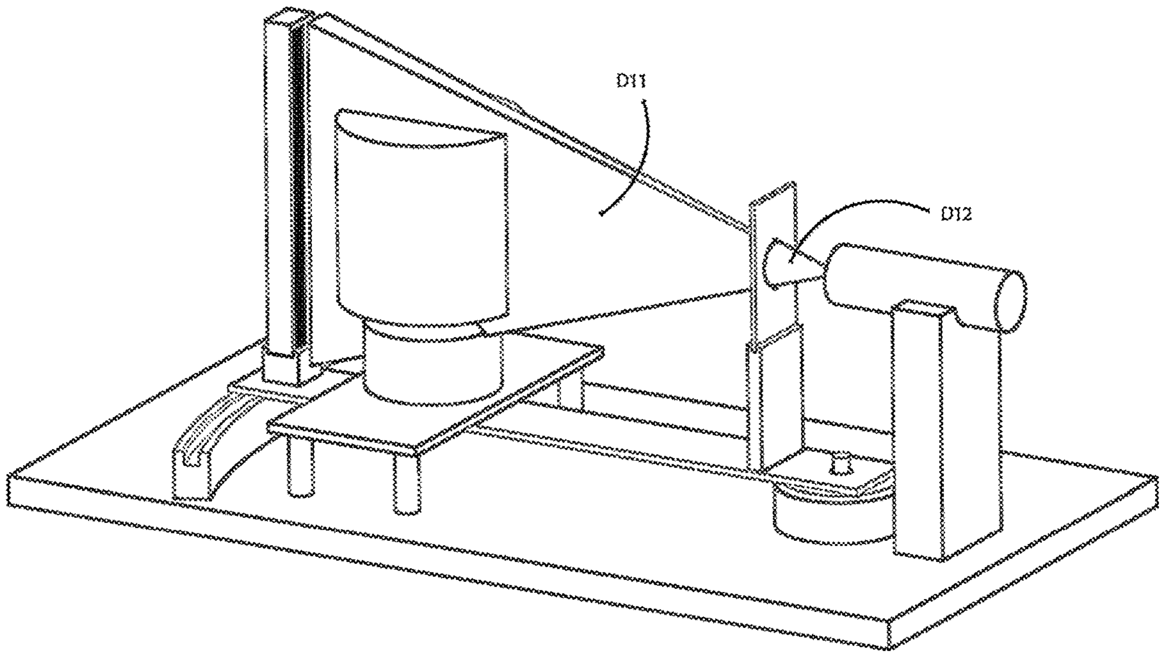
FIG. 6 depicts an X-Ray cone truncated by a collimator.
Figure 7:
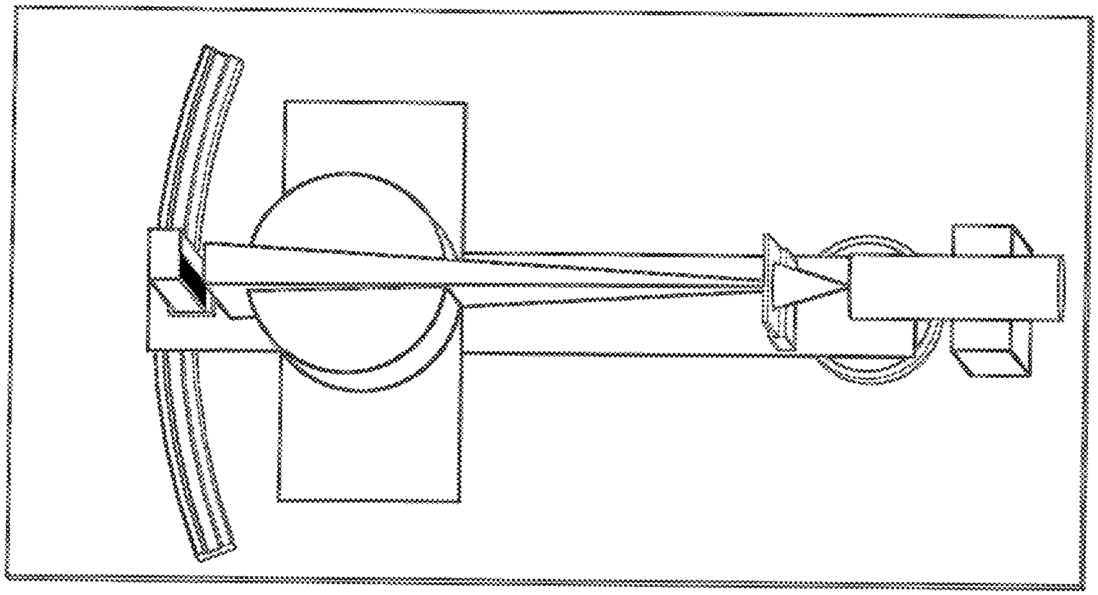
FIG. 7 depicts a top view of an X-Ray cone truncated by the collimator.

FIG. 6 shows the actual truncated X-Ray beam due to the action of the collimator. The X-Ray beam forms a full cone in the region D12, but due to the collimator preventing the X-Ray radiation from passing through other than through the slit, a thin wedge D11 is only permitted to pass through the sample and become incident on the TDI line array camera. FIG. 7 shows the same process from a top view. Note that preferably the collimator is configured (slit width, height and thickness of the collimator) so that enough of a wedge remains to fully illuminate all the pixels of the imaging but no more than necessary for the reasons noted in the previous paragraph.

Figure 8:
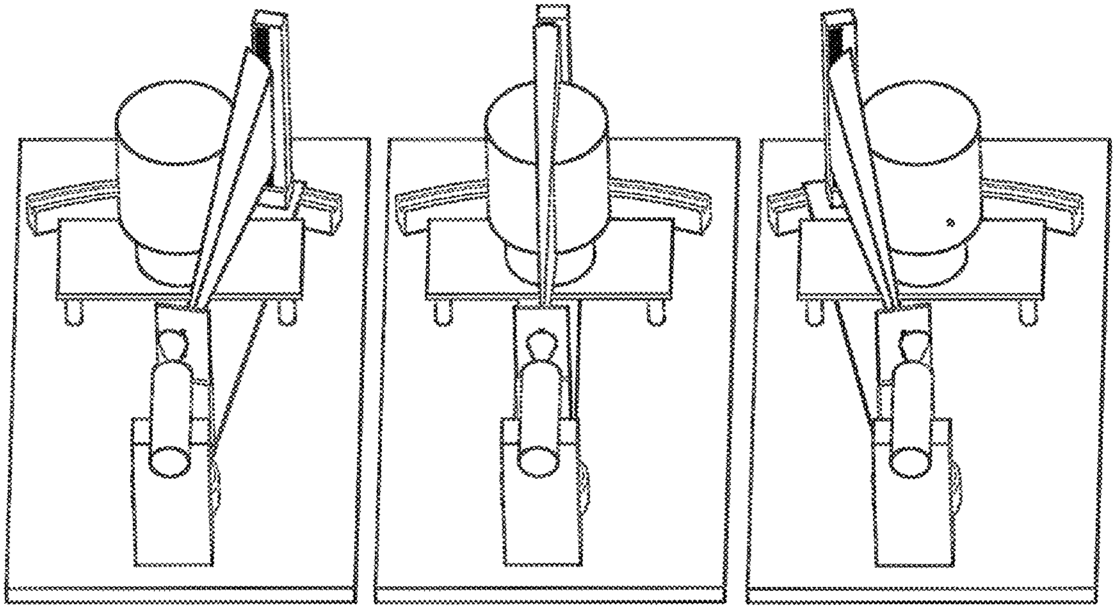
FIG. 8 depicts scanning using the TDI line array camera system of this disclosure.

FIG. 8 shows the actual scanning process of this disclosure using the TDI line array camera. In particular, the rotary stage D9 is caused to rotate so that the TDI line camera images the X-Ray projected image. Note that the projected image is not changing because the sample is stationary and the X-Ray source is also stationary. All that is changing is that the collimator is occluding the unused and unneeded X-Rays other than those incident on the imaging area. This scanning process can be performed very rapidly since the read out of the TDI line camera is done on the order of 25 KHz. The scanning process can be done in either direction; in practice, the scanning direction preferably alternates from one scan to the next with an oscillating type motion, although this is not a requirement. An additional advantage of the collimator is it reduces the scattering of X-Rays from other parts of the sample and other parts of the apparatus and that would otherwise increase the base noise level in the TDI camera and the total accumulated dose in the sample.

Figure 9:
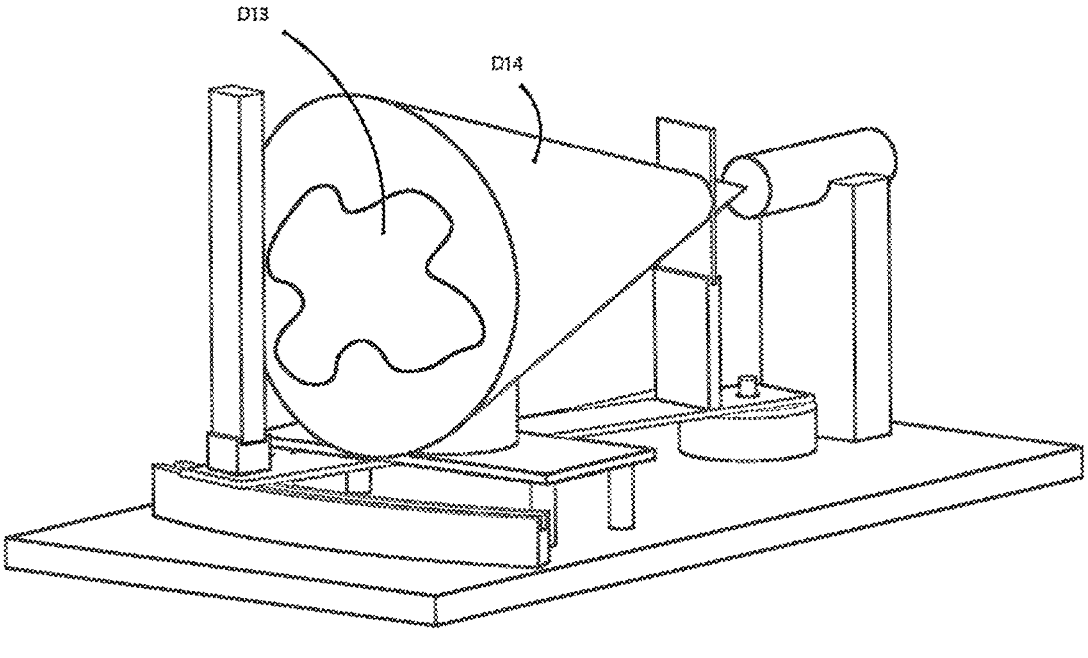
FIG. 9 depicts a final assembled cone beam approach using the described approach herein.
Figure 10:
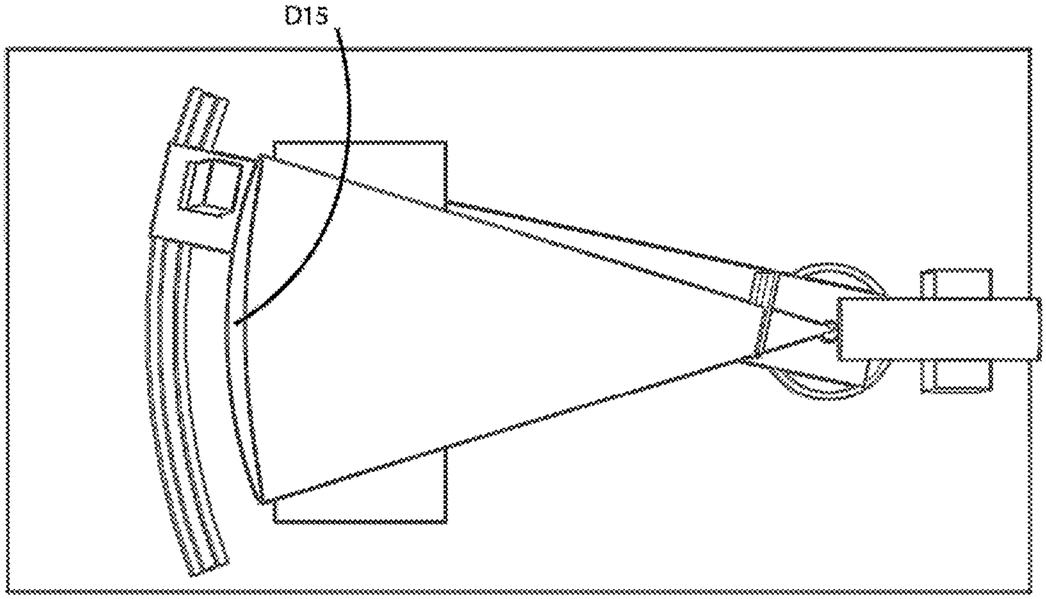
FIG. 10 depicts a curved cone beam image.

During each scan, and as depicted in FIG. 9, an image is assembled into a single image D13, which represents the radiographic projection of the sample onto that surface and effectively images the equivalent cone beam ray D14. Because of the way the TDI line camera sweeps across the view on a constant radius with respect to the X-Ray source, and as depicted in FIG. 10, the image actually lies on a curved surface D15, and not the typical flat surface of a conventional cone beam imaging system with a flat 2D detector panel. This difference is taken into account when performing the reconstruction process later.

Figure 11:
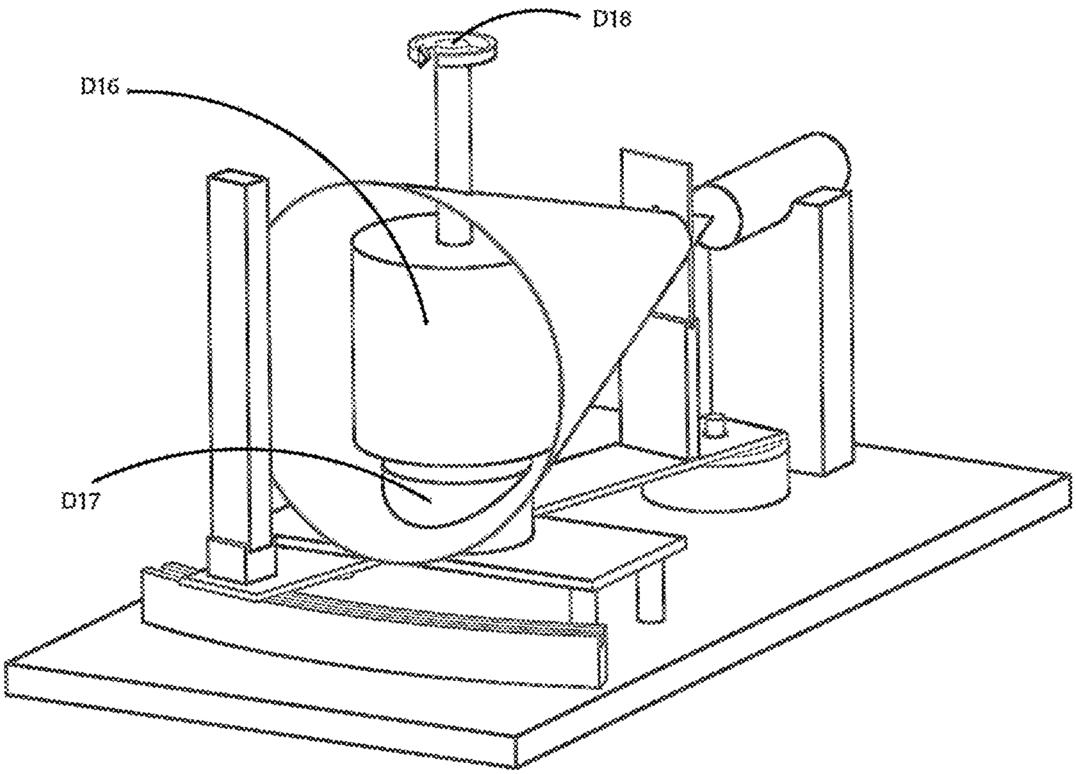
FIG. 11 depicts rotation of a sample to obtain multiple views from different angles.

The process described above produces a single cone beam image equivalent for a single sample orientation. To obtain multiple cone beam images, the following process is implemented. Referring to FIG. 11, the scanning volume D16 containing the sample is rotated by causing the rotary stage D17 to be rotated. The axis of rotation is shown by D18. The scanning process proceeds by then repeating the scan of the TDI line array as described above. Typically, a small angle is used so that there are several hundred such cone beam images generated. The rotation range is ideally performed over a full 360 degrees, but it may be less. For example, a good reconstruction can be obtained using only a 180 degree range of rotations, which in turn then halves the amount of X-Ray radiation required.

Figure 12:
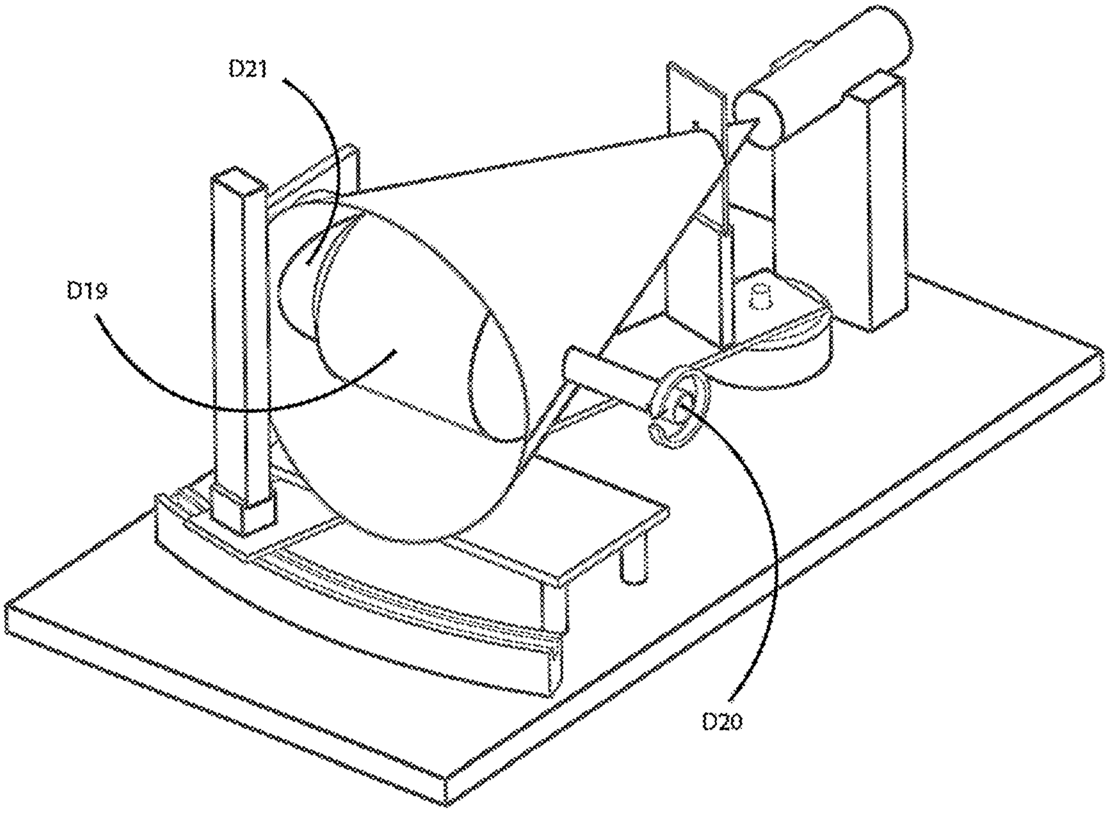
FIG. 12 depicts an alternative rotation axis for the sample shown in FIG. 11.

Because the cone beam shape is symmetric, the rotation axis for the sample may be changed. For example, and as shown in FIG. 12, the rotary stage D21 is rotated to the side so that the scanning volume D19 containing the sample is also rotated. D20 now shows the new axis of rotation. Other angles are also possible. Equivalently, and as noted above, the system may be implemented so that the sample itself is kept stationary, and the entire assembly rotates around the sample. This would be the preferred method for scanning a patient. The scanning process in that case identical to what has been described above.

Once the cone beam images have been assembled, the computation to produce a volumetric reconstruction from those cone beam images is well-understood. For example, and without limitation, the reconstruction can be performed using the fast FDK algorithm, or it may be performed using algebraic methods such as SIRT, SART, CGLS, and the like. These algorithms typically are implemented in software, namely, as a set of computer program code instructions, and that are executed in one or more hardware processors of a computing system. Machine learning techniques may be leveraged during such processing.

Vertical Transverse CT Scanning with a Line Array Camera

Figure 13:
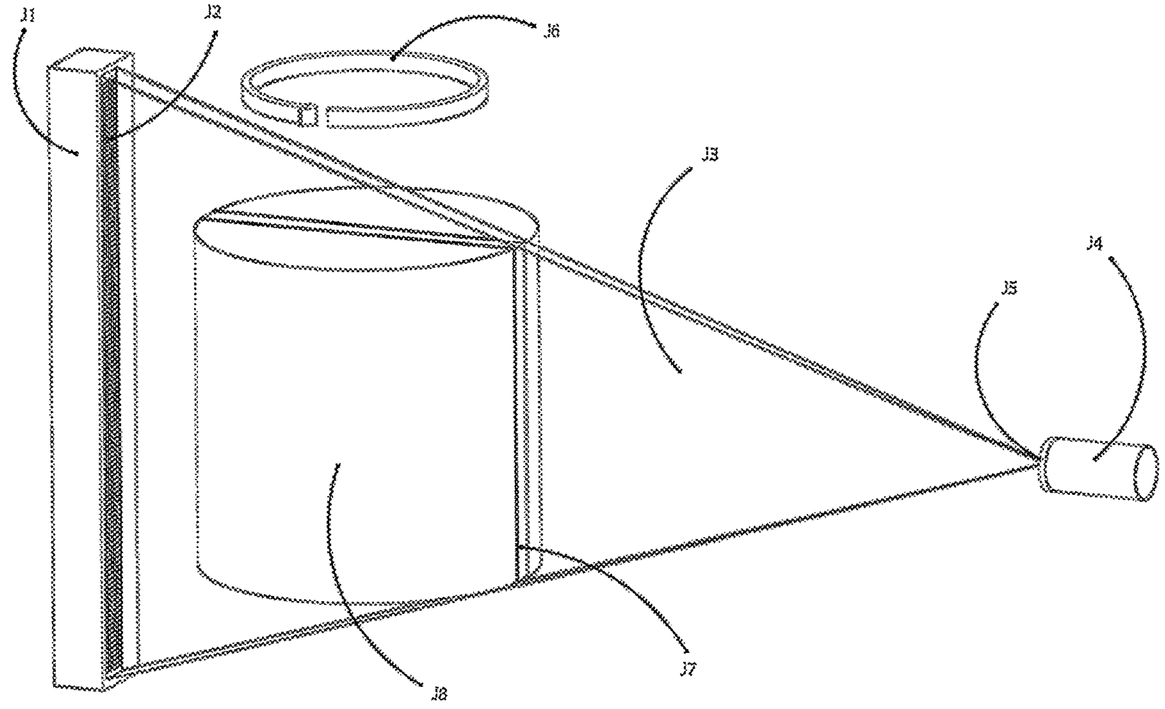
FIG. 13 depicts vertical transverse CT scanning in an alternative embodiment wherein the TDI camera is replaced with a line array camera.

While the use of the TDI camera as described above is advantageous, the techniques herein may also be practiced with any line array camera. To that end, the following describes an alternative transverse scanning technique using a line array camera. Referring to FIG. 13, in this configuration the line array camera J1 is aligned as shown with the long axis parallel to the rotate axis J6 of the sample. As discussed earlier, the cases where the sample rotates are considered as equivalent to the case where the sample remains stationary and all the other components rotate around it. As before, the sample is contained inside a scanning volume J8 which has a cylindrical shape. The X-Ray source J4 produces rays which pass through a slit collimator J5 which is configured to produce a thin wedge X-Ray beam J3. The X-Ray beam is passes through the scanning sample and produces a projection of the slice J7 of the scanning volume onto the active scanning area J2 of the line array camera. From one time step to the next, the sample is rotated as shown by the arrow J6. Thus, when an entire rotation is completed, a single 2D image is produced representing a panoramic radiographic image. For a given position of the X-Ray source and line array camera, more than one revolution may be used and the panoramic images thus obtained superimposed to increase image sensitivity. Similar to the case described earlier with the TDI line camera, a lower power X-Ray could be used to produce a more sensitive higher contrast image at the expense of increased scanning time due to the extra rotation.

Figure 14:
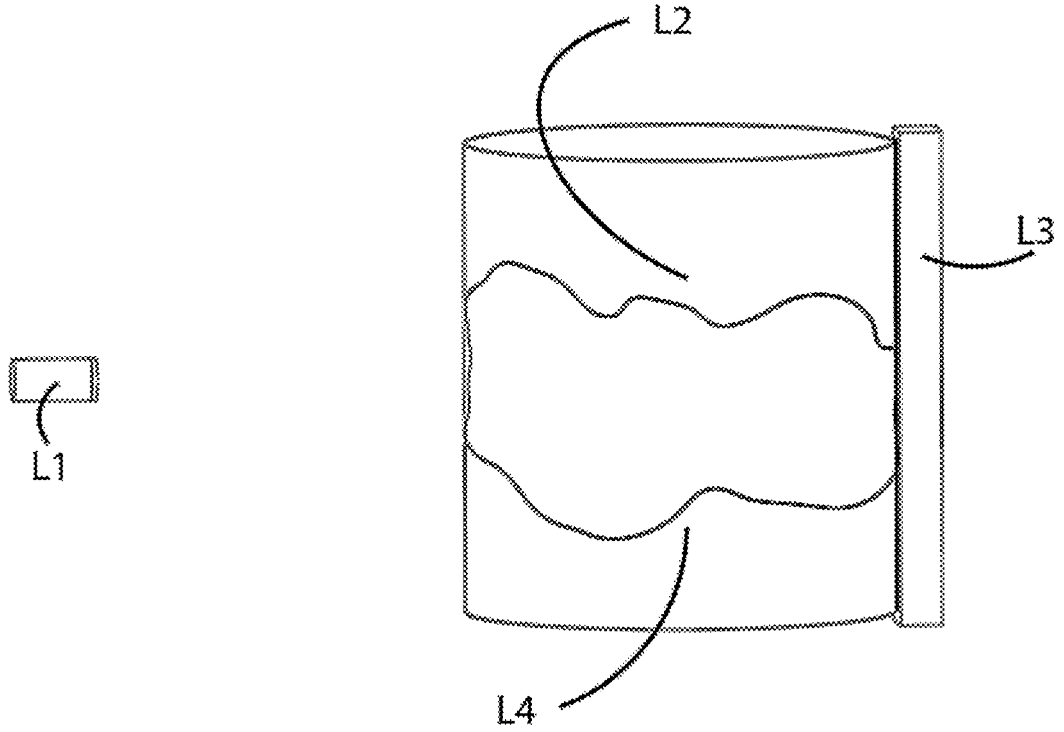
FIG. 14 depicts a panoramic radiograph image assembled from the 360° rotation of a sample.

FIG. 14 shows the panoramic image L2 that is obtained by assembling the line pixels from the line array camera L3. The x-ray source is L1. The vertical resolution is equal to the resolution output of the line array camera. In the example shown, this is a resolution of 128 pixels. The horizontal resolution depends on the pixel resolution of the line array camera as well as the rotation speed of the sample relative to the line array camera. In FIG. 14, the gray scale radiograph image projection is shown as L4. In general, this image output resembles a panoramic radiograph projection view of the sample. A single such panoramic image from a 360° rotation and scan of the sample is not sufficient to reconstruct a volume. It is also necessary to perform an additional step. In particular, after each rotation, an additional rotation is performed so that the center of rotation in the scanning volume is changed. This is necessary so that each point in the volume can have multiple rays passing through it at different angles. This is a requirement for the reconstruction algorithms.

Figure 15:
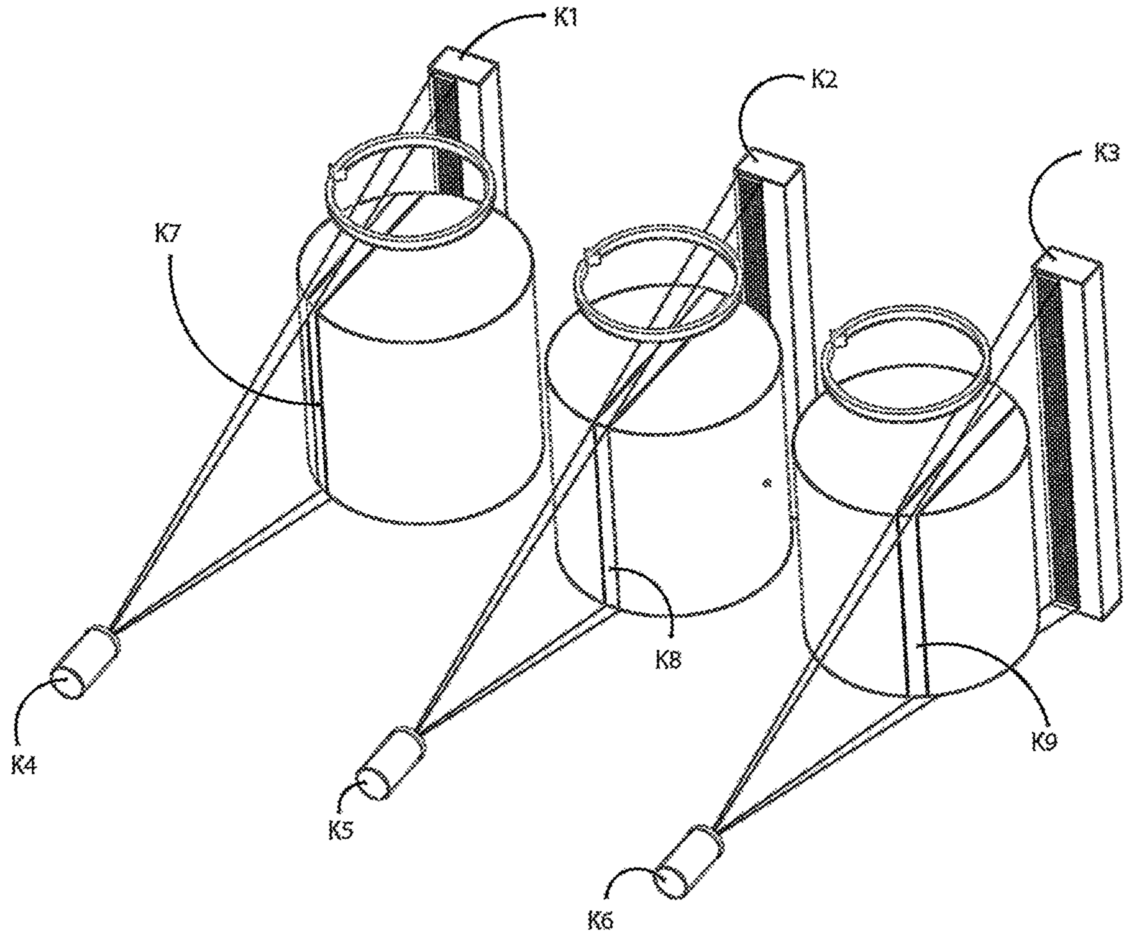
FIG. 15 depicts transverse beam shaping after each rotation scan.

By way of example, FIG. 15 shows this process for three such rotations or shifts. In practice, there will be as many as several hundred such operations so that every or the majority of small neighborhoods inside the sampling volume will be imaged with multiple rays. In addition, the extreme points or limits should start with the wedge rays being just outside the volume so that the entire scanning volume is sampled. In the example shown in FIG. 15, K1 shows the position of the line array for the first position scan. The X-Ray source K4 is also rotated so that the thin wedge x-ray beam is incident on the imaging area of the line array camera. For this configuration, the slice K7 is projected on the viewing area. In this position, the sample is then rotated for a full 360 degree view to obtain a panoramic radiograph image for that position. The line array is then rotated to position K2, and the X-ray source is also adjusted to position K5 so that the slice K8 of the sampling volume is projected. In this example, this is then repeated with the line camera position as shown by K3 (along with x-ray source to K6) and the slice K9 is projected on the sampling area. This additional scanning step can be achieved in a number of different ways. The X-Ray source and line array camera can be considered to be a rigid assembly, and could be rotated about an axis located at or near the X-ray source, or may be rotated about an axis located at or near the line camera.

Figure 16:
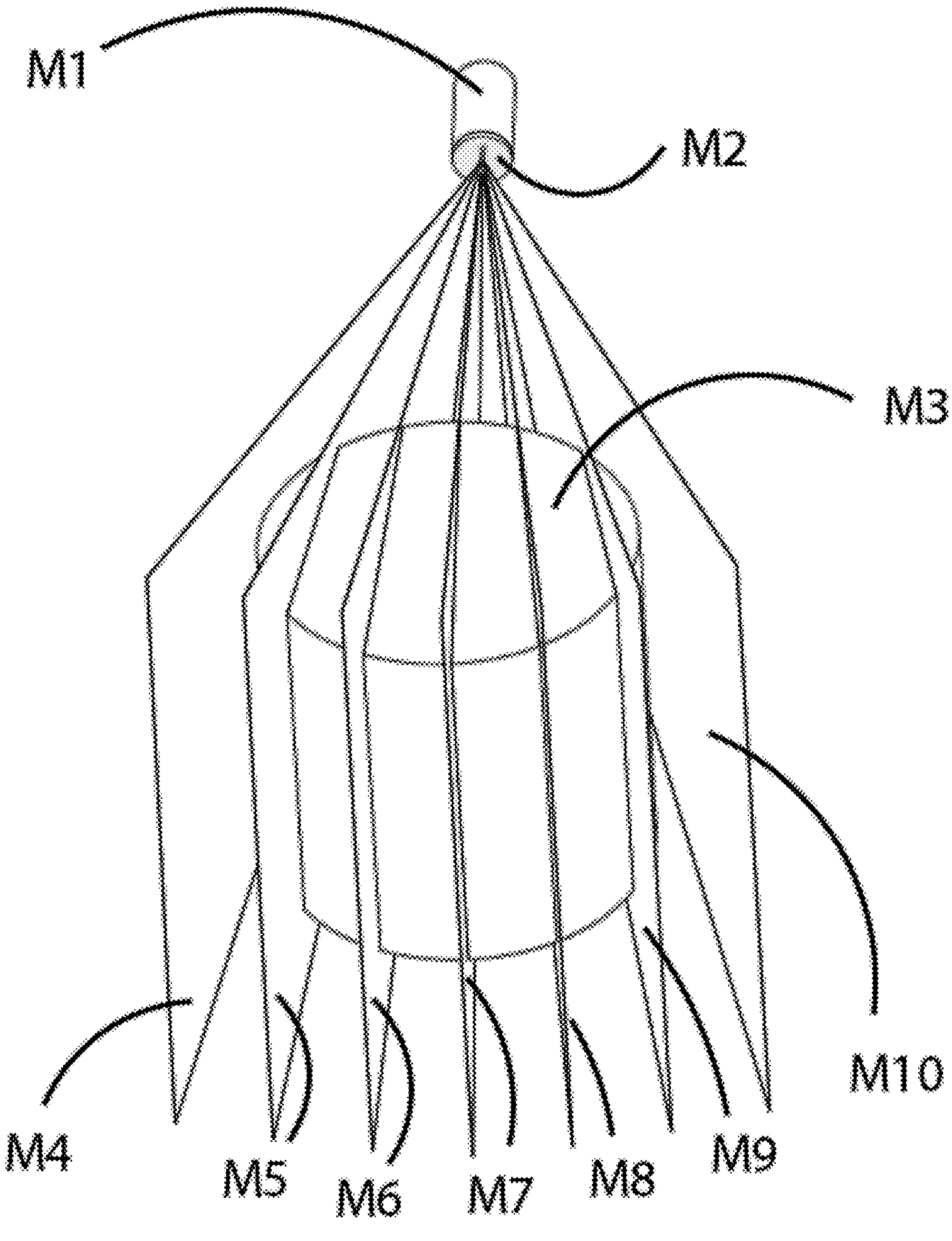
FIG. 16 depicts assembling an equivalent cone beam image for a given sample rotation angle.
Figure 17:
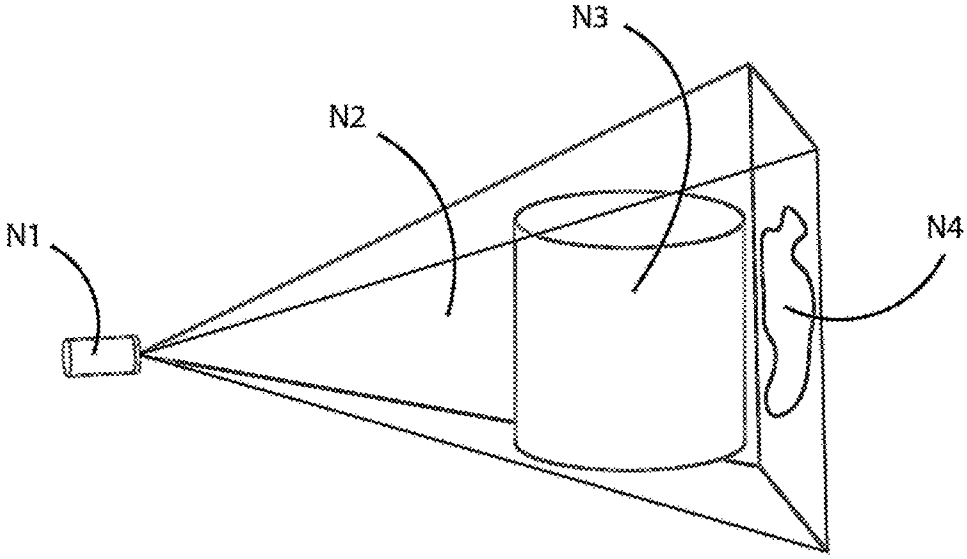
FIG. 17 depicts an equivalent cone beam image constructed from multiple panoramic images.

With reference now to FIG. 16, the following describes volume reconstruction from the vertical transverse beam CT scanning. Assuming the shifting rotation as described is performed N times, then the system has assembled N panoramic images by rotating and scanning with the line array camera for each shift rotation. Each column of the panoramic image can be associated with a particular sample angle, which can be computed by knowing the sampling rate of the line array camera and the known speed of rotation of the sample. In FIG. 16, this process is demonstrated for a particular sample rotation angle and for the demonstration (but non-limiting) case where N=7. Each column of the panoramic image, for example column 0, represents an equivalent thin ray from the point X-ray source M1 with a known angle. In the case of column 0, this known angle will be zero degrees assuming that the origin of the sample rotation was set to zero for the first scan. Using the example line array camera with a long axis resolution of 128 pixels, Panoramic image 1 provides a 128 pixel linear sampling for thin ray M4 from column 0 of that image. Panoramic image 2 provides another 128 pixel linear sampling for thin ray M5 from column 0 of that image, and so on for the remaining rays M6, M7, M8, M9 and M10. In practice, N is a much larger number, possible in the hundreds. As can be seen then, the assembly of all the column 0 values from all the panoramic images, then produces an approximation to an equivalent cone beam image for that angle. In this way, for each column of the panoramic images, the system calculates an equivalent cone beam image for that angle. FIG. 17 shows an example of the equivalent cone beam image with a grayscale radiograph projection N4 of the sample contained inside the scanning volume N3. The equivalent cone beam type scan N2 was never performed, but has been constructed from all the images. N1 is the x-ray source as before. Typically, there will be several hundred of these cone beam images corresponding to different sample rotation angles. Once the data set has been converted to the equivalent layout of a typical CBCT cone beam data set, volume reconstruction is then performed in both cases using the above-identified techniques used for CBCT cone beam reconstruction.

Figure 18:
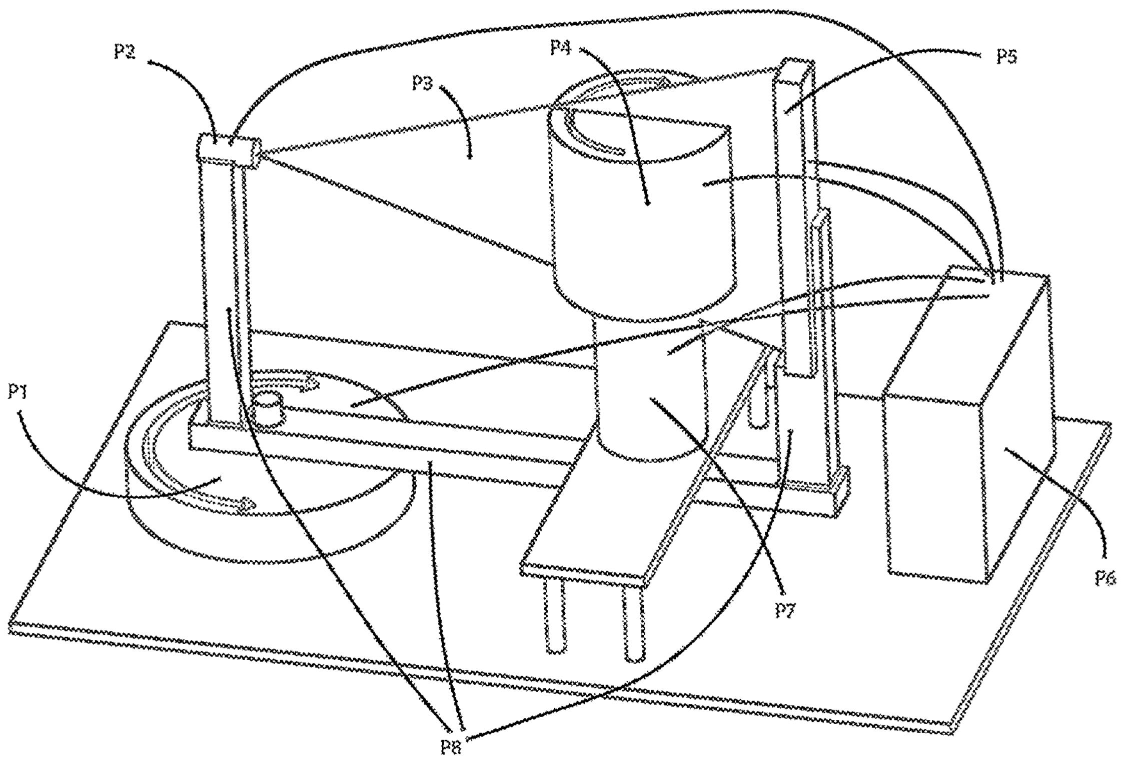
FIG. 18 depicts a system for performing a vertical transverse beam CT scan of a sample using a multiple panoramic image scanning approach.

With the above as background, FIG. 18 depicts a system for vertical transverse beam CT scanning according to the second embodiment. In this example, the scan volume is rotated, however, in most medical type applications the scan volume (for example a portion of a patient) remains stationary and instead the entire scanning assembly rotates around the scan volume. As already noted, the process is both cases is equivalent, so for ease of explanation the following shows the case where the sample is rotated.

In particular, and in the system shown in FIG. 15, there are two moving parts. The first is a rotary stage P1 to which is connected a rigid arm P8. The rigid arm in turn has mounted to it the X-Ray source P2 with slit collimator and the line scan camera P5. By rotating the stage P1 back and forth, the scan operation as shown in FIG. 16 is performed. There are other ways to achieve this motion, for example a linear stage with a linkage on the arm side near the line array camera P5 could be used. The second moving part is another rotary stage P7, which is used to rotate the scanning volume P4 and the sample contained within it. A fan beam P3 is then caused to project through the volume P4 onto the line array camera P5. A computer P6 is used to control the motion of the stages P1 and P7, to control the X-Ray source P2, and to acquire the line of pixels from the line array camera P5. The computer P6 also contains software and a software algorithm to acquire and process the images into a volumetric reconstruction of the sample, and it has a storage capacity for storing the reconstructed volume. The computer also has the means to transmit the volumetric reconstructions via hardwired or wireless network connections to other locations.

Figure 19:
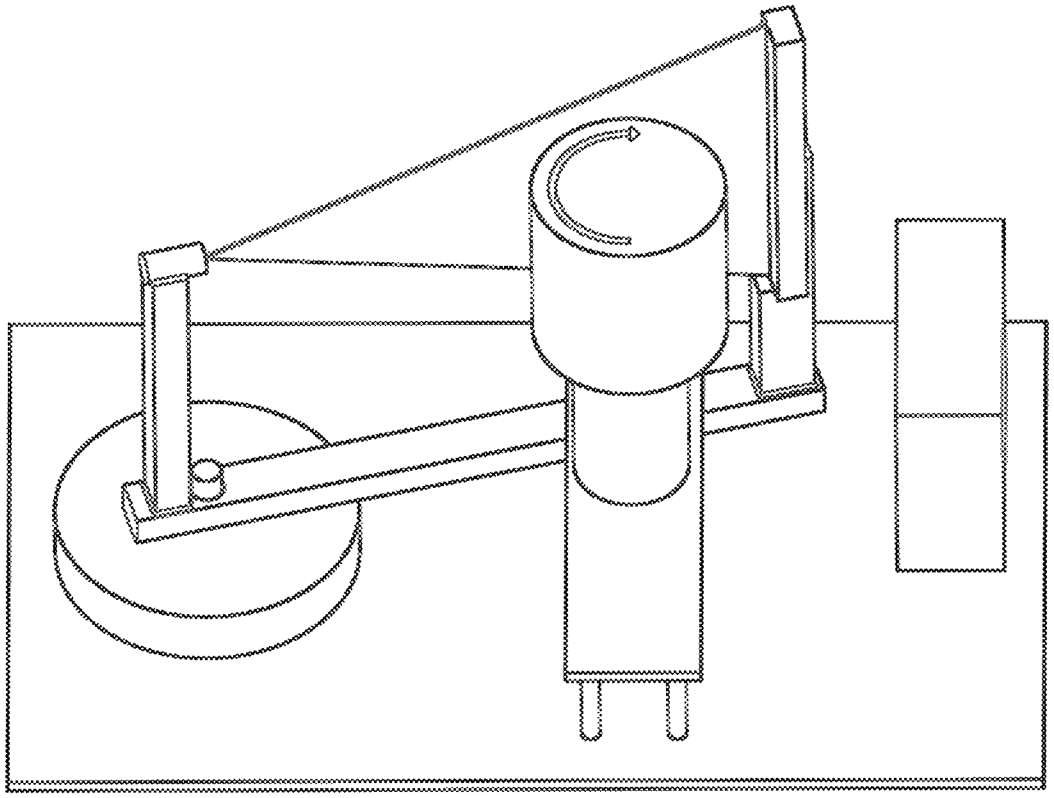
FIG. 19 depicts a starting position of the system for a first panoramic scan.
Figure 20:
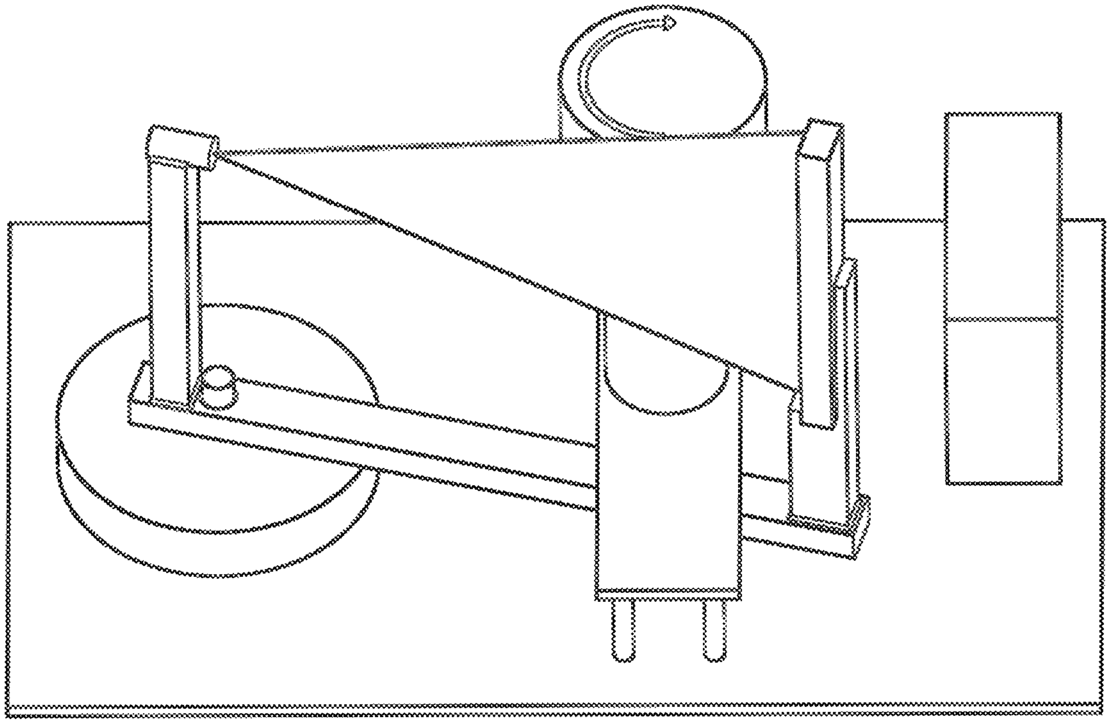
FIG. 20 depicts an ending position of the system for a final panoramic scan.

FIG. 19 depicts a starting position of the system components for a first panoramic scan. This is the same system as described for FIG. 18, the only difference being that the rotary stage P1 has been rotated so that the x-Ray beam P3 is just outside or touching the scanning volume P4. Referring to FIG. 16, this position corresponds to scan M10 shown in that diagram. As described earlier, a single panoramic scan is then performed in that configuration. The rotary stage P1 is then caused to rotate by a small amount, and the process is repeated to obtain another panoramic image. This continues until the final position shown in FIG. 20. This ending position corresponds to the scan M4 in FIG. 16.

Typically, an electronic control system is used to control the operation of any of the above-described systems. To this end, one or more computers (e.g., servers, network hosts, client computers, integrated circuits (CPUs, GPUs, and the like), microcontrollers, controllers, field-programmable-gate arrays, personal computers, digital computers, driver circuits, or analog computers) are programmed or specially adapted to perform control tasks, such as: controlling the operation of, or interfacing with, the above-described components, by controlling servo motors via closed loop control, controlling timing of steps taken by stepper motors and timing of images projected; controlling operation and intensity of X-Ray sources, receiving data from, controlling, or interfacing with one or more sensors; and performing other calculations, computations, programs, algorithms, or computer functions as necessary to facilitate control over the above-described process. For example, software in the control system enables real-time relative positioning of the various components, and real-time generation of the volume reconstruction(s). The software comprises one or more application programs, databases, utilities, processing threads, and the like, executed or executable in one or more hardware processors. Such a computer program may be stored in a non-transitory computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus. The control system components may be located remotely from other system components.

More generally, the control aspects of the techniques described herein are provided using a set of one or more computing-related entities (systems, machines, processes, programs, libraries, functions, or the like) that together facilitate or provide the described functionality described above. In a typical implementation, a representative machine on which the software executes comprises hardware (CPUS and GPUs), an operating system, an application runtime environment, and a set of applications or processes and associated data, which provide the functionality of a given system or subsystem. As described, the functionality may be implemented in a standalone machine, or across a distributed set of machines.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the subject matter herein describes improving CT scanning within dentistry, the same approach can be applied to other fields.

What is claimed is set forth below.

The invention claimed is:

1. An apparatus, comprising:

a first rotation stage;

a sample holder coupled to the first rotation stage, the sample holder holding a sample;

an X-ray source that emits a cone beam of radiation;

an assembly comprising a rigid arm having a first end portion, a second end portion, a collimator supported on the rigid arm adjacent the first end portion and between the X-ray source and the sample holder, and a line array detector including an active imaging area supported on the rigid arm adjacent the second end portion;

a second rotation stage having an axis and connected to the rigid arm adjacent the first end portion, the rigid arm configured to rotate about the axis to sweep the active imaging area of the line array detector on a constant radius with respect to the X-ray source during a scan; and a computing entity comprising hardware and software that controls rotations of the first rotation stage and the second rotation stage, retrieves line images generated from the line array detector, and reconstructs a volumetric representation of the sample based on the retrieved line images.

2. The apparatus as described in claim 1, wherein the line array detector is a time-delay integration detector.

3. The apparatus as described in claim 2, wherein the line array detector comprises a first number of pixels $n_x$ in a first direction, and a second number of pixels $n_y$ in a second direction orthogonal to the first direction, wherein $n_y$ is greater to or equal to 1, and $n_x$ is at least one order of magnitude larger than $n_y$.

4. The apparatus as described in claim 1, wherein the sample is holder supports a dental item.

5. The apparatus as described in claim 1, wherein, relative to the line array detector supported on the rigid arm that is configured to rotate about the axis, the X-ray source is fixed.

6. The apparatus as described in claim 1, wherein the collimator comprises a slit, the collimator configured to receive the cone beam of radiation and to pass through the slit only a wedge-shaped beam, the wedge-shaped beam being incident on the active imaging area.

7. The apparatus as described in claim 1, wherein the first rotation stage has an axis that is positioned parallel to the axis of the second rotation stage.

8. The apparatus as described in claim 1, wherein the first rotation stage has an axis that is positioned orthogonal to the axis of the second rotation stage.

9. The apparatus as described in claim 1, wherein the X-ray source is a microfocus device.

10. A method of imaging, comprising:

positioning a sample between an X-ray source and a line array detector;

collimating x-rays from the x-ray source into a wedge-shaped beam;

passing the wedge-shaped beam through the sample as the line array detector reciprocates along an arc to generate a plurality of line images;

assemble a first subset of the plurality of line images into a first 2D image;

assemble an $n^{th}$ subset of the plurality of line images into an $n^{th}$ 2D image, wherein a total number of subsets and corresponding 2D images is more than 2; and processing the corresponding 2D images into a 3D volumetric representation of the sample.

11. The method as described in claim 10, wherein the X-ray source approximates a point source with a finite size.

12. The method as described in claim 11, wherein an X-ray assembly including the X-ray source and the line array detector rotate about an axis passing through the point source such that each line image of the plurality of line images is obtained at a different rotation.

13. The method as described in claim 10, wherein the corresponding 2D images are processed into the 3D volumetric representation of the sample using a Cone Beam Computed Tomography (CBCT) algorithm.

14. The method as described in claim 10, wherein the sample is rotated about an axis through the sample and perpendicular to the wedge-shaped beam such that each line image of the plurality of line images is obtained at a different rotation.

15. The method as described in claim 10, wherein each of the first 2D image and the $n^{th}$ 2D image is a 2D image that is obtained at a particular rotational position of the sample relative to an X-ray assembly including the X-ray source and the line array detector.

16. The method as described in claim 10, wherein the line array detector is a time-delay integration detector.

17. The method as described in claim 10, wherein the sample is a dental item.

18. The method as described in claim 10, wherein the line array detector is associated with a first rotation stage, and wherein the sample is associated with a second rotation stage, and wherein the $n^{th}$ subset of the plurality of line images is obtained by one of: (i) keeping the second rotation stage at a constant rotation angle while a rotation angle of the first rotation stage is varied for each line image, and (ii) keeping the first rotation stage at a constant rotation angle while a rotation angle of the second rotation stage is varied for each line image.

19. The method of claim 18, wherein the plurality of line images is obtained by one of: (i) varying the rotation angle of the second rotation stage; and (ii) varying the rotation angle of the first rotation stage.

* * * * *